(12) United States Patent
Bleeker et al.

(10) Patent No.: US 7,433,033 B2
(45) Date of Patent: Oct. 7, 2008

(54) INSPECTION METHOD AND APPARATUS USING SAME

(75) Inventors: Arno Jan Bleeker, Westerhoven (NL); Vadim Yevgenyevich Banine, Helmond (NL); Johannes Onvlee, s-Hertogenbosch (NL); Jacques Cor Johan Van der Donck, Alphen aan den Rijn (NL); Michiel Peter Oderwald, Delft (NL)

(73) Assignee: ASML Netherlands B.V., Veldhoven (NL)

( * ) Notice: Subject to any disclaimer, the term of this patent is extended or adjusted under 35 U.S.C. 154(b) by 162 days.

(21) Appl. No.: 11/418,454

(22) Filed: May 5, 2006

(65) Prior Publication Data

US 2007/0258086 A1 Nov. 8, 2007

(51) Int. Cl.
*G01N 21/00* (2006.01)
(52) U.S. Cl. ............... 356/237.2; 356/237.3; 356/237.4
(58) Field of Classification Search ............. None
See application file for complete search history.

(56) References Cited

U.S. PATENT DOCUMENTS

| | | | |
|---|---|---|---|
| 5,233,191 A | 8/1993 | Noguchi et al. | 250/306 |
| 5,659,390 A * | 8/1997 | Danko | 356/237.4 |
| 5,883,710 A | 3/1999 | Nikoonahad et al. | 356/237.2 |
| 6,076,465 A | 6/2000 | Vacca et al. | 101/481 |
| 6,081,325 A | 6/2000 | Leslie et al. | 356/237.2 |
| 6,538,730 B2 | 3/2003 | Vaez-Iravani et al. | 356/237.2 |
| 6,590,645 B1 | 7/2003 | Chen et al. | 356/237.2 |
| 6,614,520 B1 | 9/2003 | Bareket et al. | 356/237.3 |
| 6,621,570 B1 | 9/2003 | Danko | 356/237.4 |
| 6,686,602 B2 * | 2/2004 | Some | 250/559.45 |
| 6,797,975 B2 | 9/2004 | Nishiyama et al. | 250/559.04 |
| 6,862,491 B2 | 3/2005 | Levin et al. | 700/121 |
| 6,879,391 B1 | 4/2005 | Danko | 356/237.4 |
| 6,985,220 B1 | 1/2006 | Chen et al. | 356/237.5 |
| 6,999,611 B1 | 2/2006 | Lopez et al. | 382/144 |
| 2002/0196433 A1 | 12/2002 | Biellak et al. | 356/239.1 |
| 2003/0184739 A1 | 10/2003 | Wilk et al. | 356/237.1 |
| 2003/0223058 A1 | 12/2003 | Leong et al. | 356/237.2 |
| 2004/0016896 A1 | 1/2004 | Almogy et al. | 250/559.45 |
| 2004/0036864 A1 | 2/2004 | Zhao et al. | 356/237.2 |
| 2004/0042002 A1 | 3/2004 | Roncone et al. | 356/237.5 |
| 2004/0066507 A1 | 4/2004 | Kren et al. | 356/237.4 |
| 2004/0095573 A1 | 5/2004 | Tsai et al. | 356/237.5 |

(Continued)

FOREIGN PATENT DOCUMENTS

JP 9-064136 A2 3/1997

(Continued)

*Primary Examiner*—Michael P Stafira
(74) *Attorney, Agent, or Firm*—Sterne, Kessler, Goldstein & Fox P.L.L.C.

(57) ABSTRACT

The invention relates to a method and device of inspecting contamination particles on an object comprising a patterned structure. The device includes a radiation system for directing a radiation beam to the object. The object is configured to scatter the beam. The device also includes an optical system arranged to receive scattered radiation from the object, and a filter provided in the optical system. The filter is associated with the patterned structure so as to filter out radiation from the scattered radiation. The device also includes a detector arranged to detect a fraction of radiation that is transmitted by the filter. Accordingly, contamination particles may be detected quickly and accurately.

15 Claims, 4 Drawing Sheets

U.S. PATENT DOCUMENTS

| | | |
|---|---|---|
| 2004/0125368 A1 | 7/2004 | Vaez-Iravani ............ 356/237.2 |
| 2004/0156042 A1 | 8/2004 | Vaez-Iravani et al. .... 356/237.1 |
| 2004/0175028 A1 | 9/2004 | Cavan ........................ 382/145 |
| 2004/0180270 A1 | 9/2004 | Heerens ......................... 430/5 |
| 2004/0201841 A1 | 10/2004 | Kim et al. ................. 356/237.3 |
| 2004/0235206 A1 | 11/2004 | Kuhlman et al. .............. 438/14 |
| 2004/0246476 A1 | 12/2004 | Bevis et al. ............... 356/237.5 |
| 2005/0018179 A1 | 1/2005 | Bevis et al. ............... 356/237.1 |
| 2005/0018182 A1 | 1/2005 | Hyun et al. ............... 356/237.4 |
| 2005/0033528 A1 | 2/2005 | Toth et al. ..................... 702/35 |
| 2005/0052643 A1 | 3/2005 | Lange et al. ............. 356/237.1 |
| 2005/0052644 A1 | 3/2005 | Lewis et al. .............. 356/237.4 |
| 2005/0094136 A1 | 5/2005 | Xu et al. .................. 356/237.3 |
| 2006/0001877 A1 | 1/2006 | Moriya ....................... 356/369 |
| 2006/0012781 A1 | 1/2006 | Fradkin et al. ........... 356/237.5 |
| 2006/0256324 A1* | 11/2006 | Den Boef et al. ........ 356/237.2 |

FOREIGN PATENT DOCUMENTS

| | | |
|---|---|---|
| JP | 2001-108411 | 4/2001 |
| JP | 2004/258384 A2 | 9/2004 |
| JP | 2005-164446 | 6/2005 |
| JP | 2005-274173 A2 | 10/2005 |
| WO | WO 03/083560 A2 | 10/2003 |
| WO | WO 2005/050132 A1 | 6/2005 |
| WO | WO 2005/101483 A1 | 10/2005 |
| WO | WO 2006/019446 A2 | 2/2006 |
| WO | WO 2006/019446 A3 | 2/2006 |

* cited by examiner

INSPECTION METHOD AND APPARATUS USING SAME

FIELD

The present invention relates to a method and device for inspecting contamination particles on a object provided with a patterned structure, in particular, an EUV reticle.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive metal compound (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

Being able to guarantee defect free imaging in extreme ultraviolet light (EUV) is an advantage for a successful introduction and acceptance in the market. Particles on the EUV reticles are one of the main sources of imaging defects. Because the EUV reticles are not covered by a membrane or pellicle (as common deep ultraviolet light (DUV) reticles have) which keeps contamination out of focus, they are prone to particle contamination, which may cause defects in a lithographic process. Cleaning and inspecting the reticle before moving the reticle to an exposure position is thus a desired aspect in a reticle handling process.

Current fast particle detection methods for DUV reticles and blanks use scattered light techniques. In this technique, a laser beam is focused on the reticle and a radiation beam that is scattered away from a specular reflection direction is inspected. In one embodiment, this is done by grazing incidence, although this is not strictly needed.

Particles on an object with a patterned surface, such as EUV reticles, will randomly scatter the light. By observing the illuminated surface with a microscope, the particles will light up as bright spots. The intensity of the spots is a measure of the size of the particle. However, these methods are not easily transferable to objects having non-flat surfaces such as an EUV reticle, because the patterned surface structure of the EUV reticle will contribute to the scattered light.

SUMMARY

It is desirable to provide a method and a device for inspecting contamination particles on an object that provide a fast and accurate inspection of the object. According to an aspect of the invention, there is provided a method for inspecting an object provided with a patterned structure for contamination particles. The method comprises directing a radiation beam to the object, receiving scattered radiation from the object, filtering radiation from the scattered radiation with a filter, and inspecting a fraction of the scattered radiation that is transmitted by the filter as representative of contamination particles on the object.

According to another aspect of the invention, there is provided an inspection device for inspecting an object provided with a patterned structure for contamination particles. The device comprises a radiation system for directing a radiation beam to the object. The object is configured to scatter the beam. The device also includes an optical system arranged to receive scattered radiation from the object, and a filter provided in the optical system. The filter is associated with the patterned structure so as to filter out radiation from the scattered radiation. The inspection device also comprises a detector arranged to detect a fraction of radiation that is transmitted by the filter.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
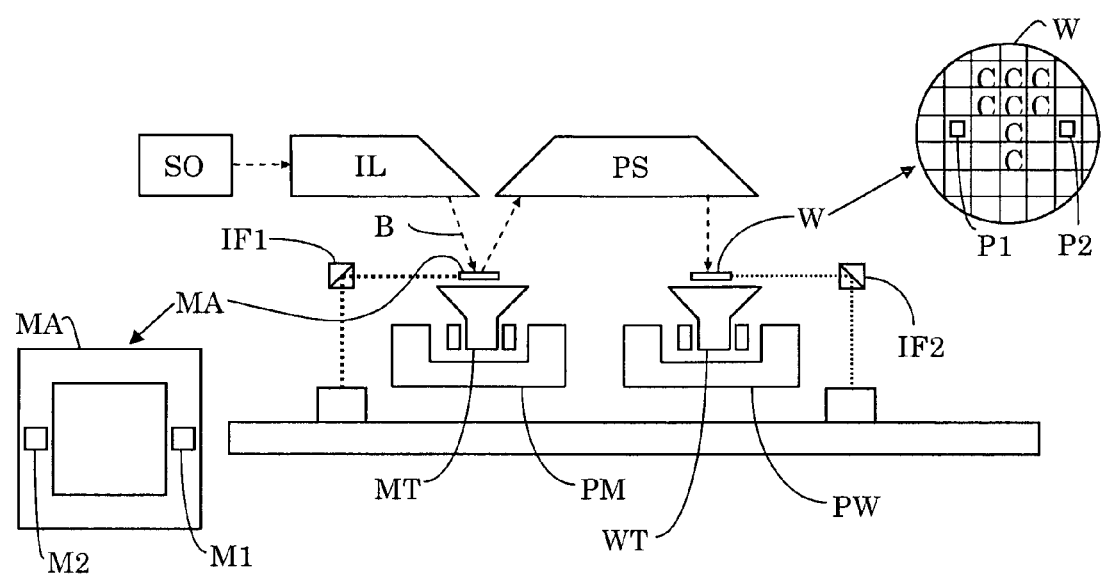
FIG. 1 depicts a lithographic apparatus according to an embodiment of the invention.

FIG. 1 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
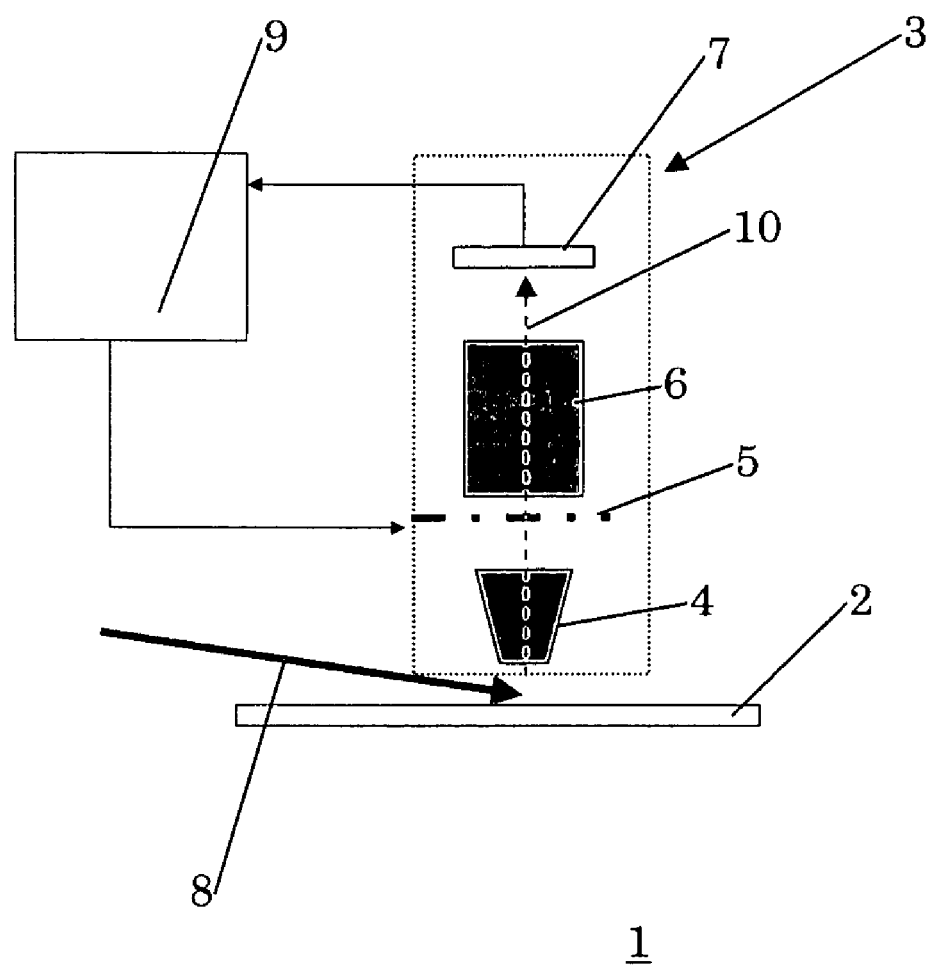
FIG. 2 shows a first embodiment of the invention.

FIG. 2 illustrates a first embodiment of the invention. The embodiment is depicted as a separate device 1 but it may optionally also be provided as an in-tool device, that is, in the lithographic apparatus as described with reference to FIG. 1. As a separate device, it may be used for inspection purposes of an object 2, which may be a mask, prior to shipping. As an in-tool device, it may perform a quick inspection of the object 2 prior to a lithographic process. In the setup of FIG. 2 there is arranged a single optical channel 3 through which both pattern analysis and particle detection signal may be collected. The channel 3 comprises a microscope objective 4, a pupil filter 5, a projection optical system 6 and an image recording system 7. A grazing incidence laser beam 8 is directed to the object 2. The wavelength of the laser beam 8 can be any wavelength suitable for inspection purposes, in particular, but not necessarily (although not excluded therefrom) EUV light. Typically, unless specified otherwise, the term "light" or "radiation" is used to indicate any electromagnetic radiation of a suitable wavelength. For the purposes of this application, in the embodiments, visible or near visible light may be used for inspection purposes.

Accordingly, in the depicted embodiment, the pupil filter 5 changes from one mode to the other mode. This embodiment may have as a benefit that the volume of the device may be limited. The device 1 is thus used in an alternating mode: in a first mode, a pattern of an object 2 is detected by a CCD or image recording system. The pattern is analyzed, by means of optical filtering and/or software filtering in a computer 9, and reversely, a filter pattern is calculated by the computer 9 to provide control signals to the adaptive filter 5 provided in a pupil plane, with control signals in order to form a selective filter for blocking optical scattering due to a predetermined pattern of the object 2.

In the filter analysis for constructing a reverse filter pattern, a scattering signal of a potential contamination particle is negligible compared to a scattering amplitude of the pattern. In addition, regularity aspects of the pattern of object 2 may be taken into account.

Then, in a second mode, the filter 5 is activated, in an adaptive mode, and scattered radiation 10 from the object 2 is selectively blocked.

Thus, a principal component in said received scattered radiation beam 10 of spectral components is derived from said received scattered radiation beam 10, and an inverse filter is constructed, derived from said principal component. When the filter 5 is in active mode, the image recording system 7 analyzes the incoming radiation beam signal as a signal that can be attributed to the presence of contamination particles, since in this condition, scattered radiation from the patterned structure is filtered out.

Accordingly, a filter 5 is provided as a spatial filter that is provided in a pupil plane relative to said object 2 so as to filter out radiation from scattered radiation scattered by the patterned structure (not shown) present on the object 5.

To lessen the constraints on dynamic range for the image recording system 7, additional optical elements may be present, so that the dynamic range from the direct scattered image is brought in accordance with the dynamic range of the residual image corresponding to potential contamination particles. The filter 5 may be a micro mirror device, such as a so-called TI-DMD, or a LCD based device, for example a so-called, LCOS, which may be used in a reflective or transmissive mode.

The adaptive filter embodiment has as an advantage that no a priori knowledge on the pattern 2 of the object is necessary. However, it is understood that the invention can also be used with a fixed filter, depending on specific application purposes.

Figure 3:
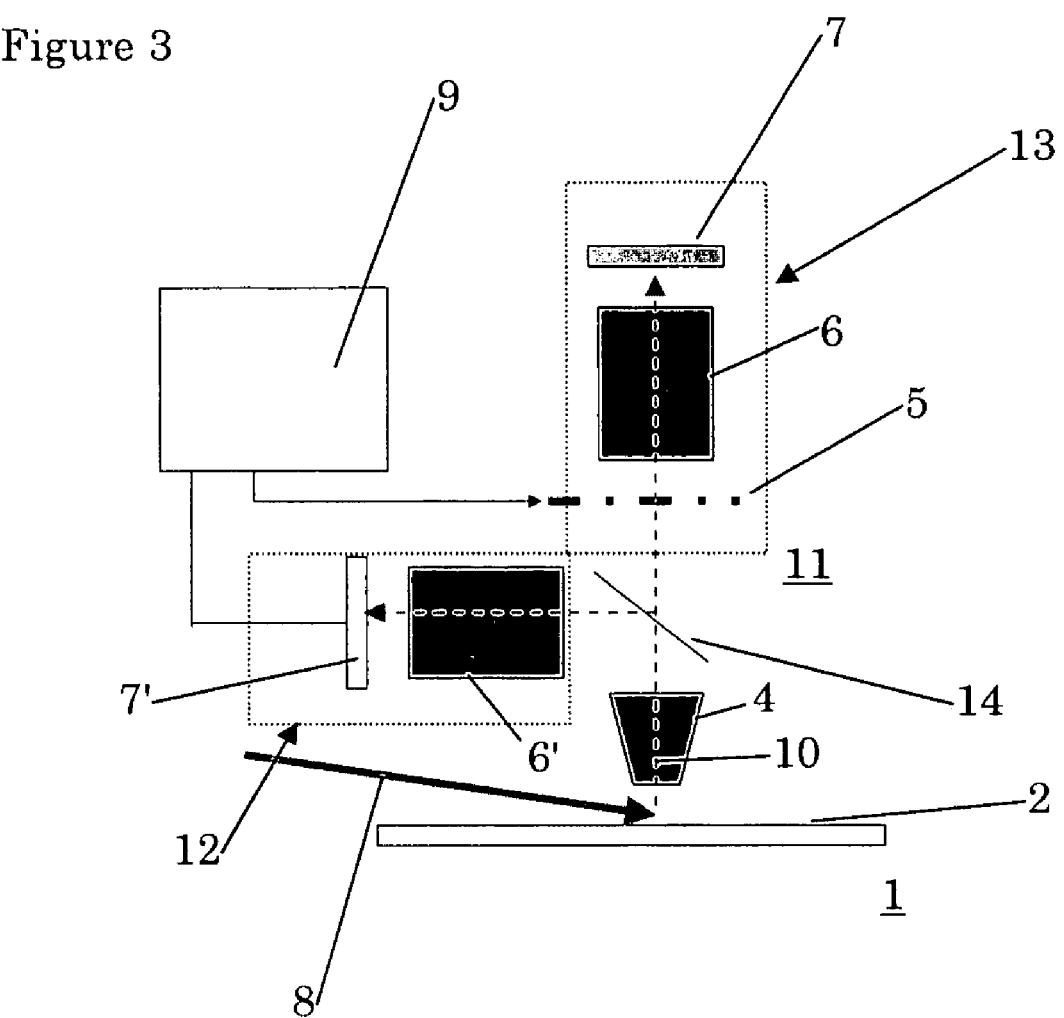
FIG. 3 shows a second embodiment of the invention.

In FIG. 3, an alternative embodiment is shown that includes an optical system 11 comprising multiple optical channels 12, 13. In particular, one channel 12 is used for the pattern analysis and one channel 13 is used for the particle detection signals. To provide the plurality of channels, in the embodiment of FIG. 3, a beam splitter 14 is used to divide the radiation intensity of scattered radiation 10 from a grazing incidence radiation beam 8 that is scattered by a patterned object 2 to an un-filtered branch that goes to one channel 12, and a filtered branch that goes to the other channel 13.

Accordingly, two image recorders 7 and 7' are present. The image recorder 7' in the non-filtered branch detects the object pattern, generally as described with reference to 2. This pattern information is used to generate the pattern on the pupil filter 5 in the particle detection branch in the optical channel 13. In comparison with FIG. 2, the present embodiment may provide a higher throughput but may require additional optical elements.

Accordingly, FIG. 3 shows an inspection device 1 comprising an adaptive filter 5 provided in the optical channel 13 of the optical system 11 for transmitting a filtered radiation beam 10. The optical system 11 comprises the further optical channel 12 that comprises a further detector 7'. The further detector 7' detects the scattered radiation beam 10 in an unfiltered condition. The further detector 7' detects a principal component in the received scattered radiation beam of spectral components derived from the received scattered radiation beam 10, and communicatively coupled to the adaptive filter 5 so as to provide an inverse filter derived from the principal component.

Since the detected radiation is of a scattered nature, the detection resolution of the image recording device 7 may be relatively low, in particular, in the order of several micrometers, so that detection may be performed relatively fast. In particular, the method circumvents the need for detailed nanometer inspection using an electron microscope for visually detecting a particle. A typical feasible analysis time could be several minutes, in particular, maximum 15 minutes, which may fit a maximum single lot expose time. Accordingly, a feasible resolution could be 1 pixel per 1 micrometer object 2, in a scanning mode of the detector 7, which would amount to about 5 minutes detection time of an entire object 2.

An alternative embodiment may be used (not shown) in which pattern detection is provided separately from a particle detection optical system. Thus, online (in tool), or offline, a pattern detection can be provided. In the offline case, the pattern data is preferably collected with a guaranteed clean reticle. In addition, this reference inspection may be more accurate (and slower) than in an online inspection. The data that is thus collected can be provided synchronized with an actual detection, so that filtering of the detection beam 10 can be provided.

Figure 4:
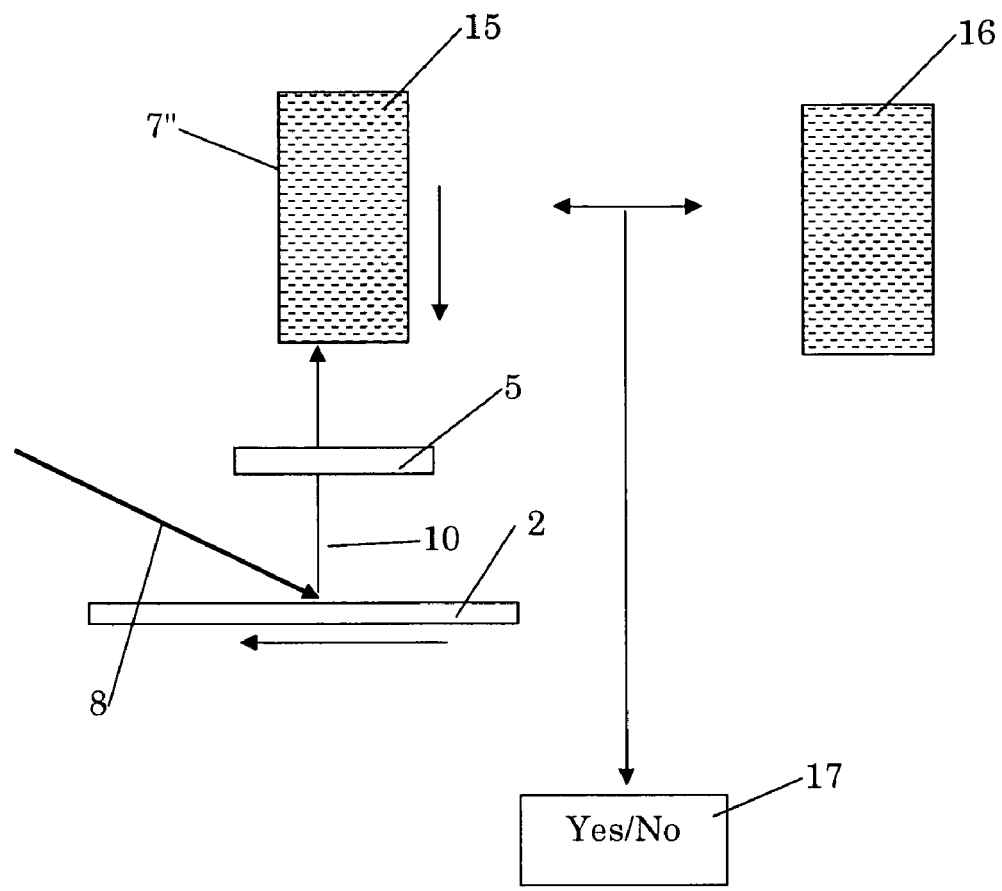
FIG. 4 shows a third embodiment of the invention.

In yet another embodiment of the invention, FIG. 4 schematically shows a method of inspecting contamination particles on an object 2 wherein another type of filtering is provided than disclosed previously. In this embodiment, a detector 7" is provided to provide a speckle pattern 15 from a scattered radiation beam 10 scattered by a patterned surface. As previously, the radiation beam 10 may be provided by a laser beam 8 of a suitable wavelength, which is oriented appropriately relative to the scattering object 2. As in the previous described embodiments, a grazing incidence angle may be used, although other angles may also be of use.

Accordingly, the generated speckle pattern 15 is representative of contamination particles on said patterned structure and can be used as a fingerprint technique. The generated speckle pattern 15 is inspected and is compared with a predetermined speckle pattern 16 that is associated with a particle free patterned surface. Thus a filtering is provided, wherein a fraction of radiation transmitted through the filtering is representative of contamination particles on said patterned structure. Based on a similarity criterion, a probability value can be derived on the presence of contamination particles on the object 2.

This value can be used in a yes/no decision 17, on whether to accept an object such as a reticle for use in lithographic processing. The criterion referenced here above may encompass a size estimate, made from an intensity difference between a measured speckle pattern 15 and the predetermined speckle pattern 16. In this way, the system may be arranged to reject the reticle when a particle is larger than a certain predetermined threshold.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Furthermore, although the illustrated embodiments suggest an orientation of the object with the patterned surface oriented opposite to the direction of gravity, the position of the object is not limited thereto and may be oriented otherwise, in particular, in an orientation wherein the patterned surface is scanned with the surface oriented along the direction of gravity. This may have as a benefit that it will minimize the risk of collecting particles during the scan process.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A method for inspecting an object provided with a patterned structure for contamination particles, said method comprising:
   directing a radiation beam to said object;
   receiving scattered radiation from said object;
   filtering radiation from said scattered radiation with a filter; and
   inspecting a fraction of the scattered radiation that is transmitted by the filter as representative of contamination particles on the object,
   wherein said filter is configured to generate a speckle difference pattern, provided by a difference of a detected speckle pattern and a predetermined speckle pattern that is associated with a particle free patterned surface, so as to detect the presence of a contamination particle.

2. A method according to claim 1, wherein said filter is associated with said patterned structure.

3. A method according to claim 2, wherein said filter is provided as a spatial filter that is provided in a conjugate plane relative to said object so as to filter out radiation from said received scattered radiation that is scattered by said patterned structure.

4. A method according to claim 2, wherein said filter is an adaptive filter.

5. A method according to claim 4, wherein said filter is adapted according to a predetermined filter pattern according to said patterned structure.

6. A method according to claim 4, further comprising:
   detecting a principal component in said received scattered radiation of spectral components derived from said received scattered radiation; and
   constructing an inverse filter derived from said principal component.

7. A method according to claim 4, wherein said filter is a micro mirror device.

8. A method according to claim 7, wherein the micro mirror device is TI-DMD or a LCD based device.

9. A method according to claim 8, wherein the LCD based device is an LCOS used in a reflective or a transmissive mode.

10. A method according to claim 1, wherein said radiation beam is provided as a grazing incidence laser beam of visible or near visible light.

11. An inspection device for inspecting an object provided with a patterned structure for contamination particles, said device comprising:
- a radiation system for directing a radiation beam to said object, which beam is scattered by the object;
- an optical system arranged to receive scattered radiation from said object;
- a filter provided in said optical system, said filter being associated with said patterned structure so as to filter out radiation from said scattered radiation; and
- a detector arranged to detect a fraction of radiation that is transmitted by the filter,
- wherein said filter is configured to generate a speckle difference pattern, provided by a difference of a detected speckle pattern and a predetermined speckle pattern that is associated with a particle free patterned surface, so as to detect the presence of a contamination particle.

12. An inspection device according to claim 11, wherein said filter is provided as an adaptive filter in a branch of said optical system, for transmitting said filtered radiation; and wherein said optical system comprises a further branch comprising a further detector; said further detector detecting said scattered radiation in an unfiltered condition, said further detector detecting a principal component in said received scattered radiation of spectral components derived from said received scattered radiation, and communicatively coupled to said adaptive filter so as to provide an inverse filter derived from said principal component.

13. A lithographic apparatus comprising:
- a support constructed to support a patterning device provided with a patterned structure, the patterning device being capable of imparting a radiation beam with a pattern in its cross-section to form a patterned radiation beam;
- a substrate table constructed to hold a substrate;
- a projection system configured to project the patterned radiation beam onto a target portion of the substrate; and
- an inspection device arranged to inspect said patterning device, said inspection device comprising
  - a radiation system for directing a radiation beam to said patterning device, said patterning device being configured to scatter said beam;
  - an optical system arranged to receive scattered radiation from said patterning device;
  - a filter provided in said optical system, said filter being associated with said patterned structure so as to filter out radiation from said scattered radiation; and
  - a detector arranged to detect a fraction of radiation that is transmitted by the filter.

14. A lithographic apparatus according to claim 13, wherein said filter is configured to generate a speckle difference pattern, provided by a difference of a detected speckle pattern and a predetermined speckle pattern that is associated with a particle free patterned surface, so as to detect the presence of a contamination particle.

15. A method for inspecting a patterning device provided with a patterned structure for contamination particles, said method comprising:
- directing a radiation beam to said patterning device;
- receiving scattered radiation from said patterning device;
- detecting a speckle pattern that is representative of contamination particles on said patterned structure; and
- comparing the detected speckle pattern with a predetermined speckle pattern that is associated with a particle free patterned surface, so as to detect the presence of a contamination particle.

* * * * *